US00PP24806P3

(12) United States Plant Patent
Olesen

(10) Patent No.: US PP24,806 P3
(45) Date of Patent: Aug. 26, 2014

(54) HYBRID TEA ROSE PLANT NAMED 'POULHT007'

(50) Latin Name: ***Rosa* hybrid**
Varietal Denomination: Poulht007

(75) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 92 days.

(21) Appl. No.: 13/507,019

(22) Filed: May 31, 2012

(65) Prior Publication Data

US 2013/0326754 P1 Dec. 5, 2013

(51) Int. Cl.
*A01H 5/00* (2006.01)

(52) U.S. Cl.
USPC ..... Plt./135; Plt./101

(58) Field of Classification Search
USPC ..... Plt./101, 130, 135, 139
See application file for complete search history.

*Primary Examiner* — Susan McCormick Ewoldt

(57) ABSTRACT

A new garden rose plant of the Hybrid Tea class which has abundant, orange flowers and attractive foliage. This new and distinct variety has shown to be uniform and stable in the resulting generations from asexual propagation.

1 Drawing Sheet

Botanical designation: *Rosa* hybrid.
Variety denomination: 'Poulht007'.

SUMMARY OF THE INVENTION

The present invention constitutes a new and distinct variety of garden rose plant which originated from a controlled crossing between the female seed parent, an unnamed seedling, and the male pollen parent, also an unnamed seedling.

The two parents were crossed during the summer of 2001 and the resulting seeds were planted in a controlled environment in Fredensborg, Denmark. The new variety, named 'Poulht007', originated as a single seedling from the stated cross.

The new variety may be distinguished from its male pollen parent and female seed parent primarily by flower coloration and growth habit.

The objective of the hybridization of this rose variety was to create a new and distinct variety for garden use with unique qualities, such as:

1. Uniform and abundant orange flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulht007' from all other varieties of which we are aware.

As part of the rose development program, Mogens N. Olesen germinated the seeds from the aforementioned hybridization during winter of 2001 and conducted evaluations on the resulting seedlings in a controlled environment in Fredensborg, Denmark. 'Poulht007' was selected in the spring of 2002 by the inventor as a single plant from the progeny of the aforementioned hybridization.

Asexual reproduction of 'Poulht007' by traditional budding and rooted cuttings was first done by Mogens N. Olesen in the nursery in Fredensborg, Denmark in July, 2002. This initial and other subsequent asexual propagations conducted in controlled environments have demonstrated that the characteristics of 'Poulht007' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulht007'. Specifically illustrated in the drawing are flowers at various stages of development, flower in parts, leaves, and stems. Illustrated plants are 2 years of age.

DETAILED DESCRIPTION OF THE VARIETY

The following is a description of 'Poulht007', as observed in its growth in in a field nursery in Bakersfield, Calif. 2 years of age, and were grown on their own roots. Color references are made using The Royal Horticultural Society (London, England) Colour Chart, 2001, except where common terms of color are used.

For a comparison, several physical characteristics of the rose variety 'Poulpmt007', U.S. Plant Pat. No. 22,714 are compared to 'Poulht007' in Chart 1.

CHART 1

| | 'Poulht007' | 'Poulpmt007' |
|---|---|---|
| Petal Count | 28 | 20 |
| Flower Diameter | 70 mm | 50 to 60 mm |
| General Tonality of Flower Color | Red Group 43B | Red Group 52B with intonations of Red-Purple Group 58B |

FLOWER AND FLOWER BUD

Blooming habit: Continuous.
Flower bud:

*Size*.—Upon opening, 30 mm in length from base of receptacle to end of bud. Bud diameter is 20 mm.

*Bud form*.—Ovoid.

*Bud color*.—As sepals divide petals are Red Group 42A.
*Sepal inner surface*.—Color: Yellow-Green Group 145B. Surface: Smooth.
*Sepal outer surface*.—Color: Yellow-Green Group 144A. Texture: Smooth.
*Sepal shape*.—Apex: Cirrhose. Base: Flat at union with receptacle.
*Sepal margin*.—Margins have weak foliaceous appendages on three of the five sepals.
*Sepal size*.—22 mm long by 10 mm wide.
*Receptacle*.—Texture: Smooth. Size: 7 mm in height by 10 mm wide. Color: Yellow-Green Group 144A. Shape: Campanulate.
*Pedicel*.—Surface: Smooth. Length: 50 mm average. Diameter: 4 mm on average. Color: Yellow-Green Group 144A. Strength: Strong.

Flower bud development: Flower buds are borne singly.

Flower bloom:
*Fragrance*.—Moderate floral perfume scent.
*Duration*.—The blooms have a duration on the plant of approximately 14 days. Petals fall cleanly away from plant after flowers have fully matured.
*Size*.—Flower diameter is 70 mm when open. Flower depth is 35 mm.
*Flower shape*.—Generally, hybrid tea shape with a tightly closed, high pointed center.
*Shape of flower, side view*.—The upper portion is flat, and the lower portions is flat.

Petalage: Under normal conditions, flowers have 28 petals total, 3 to 4 of which are petaloids.

General tonality of flower: Open flowers are Red Group 43B.

Petal color:
*Upon opening, outer and inner petals*.—Upper surface: Red Group 40A. Occasionally petals are splashed with Yellow Group 8D. Petal base is Yellow Group 12B. Lower surface: Red Group 41B. Petal base is Yellow Group 12B.
*After opening, outer and inner petals*.—Upper surface: Red Group 40A. Occasionally petals are splashed with Yellow Group 8D. Petal base is Yellow Group 12B. Lower surface: Red Group 41B. Petal base is Yellow Group 12B.

Petals:
*Petal reflex*.—Moderate.
*Margin*.—Entire and uniform. Medium undulations of margin observed.
*Shape*.—Generally rounded. Apex shape: Rounded. Base shape: Rounded.
*Size*.—40 mm (l)×40 mm (w).
*Texture*.—Smooth.
*Thickness*.—Average.

Petaloids:
*Size*.—24 mm (l) by 18 mm (w).
*Quantity*.—3 to 4.
*Shape*.—Apex is rounded, base is acute. Margins are undulated.
*Color*.—Upper, Red Group 40A, with occasional splash of Yellow Group 8D. Petaloid base is Yellow Group 12B. Lower surface: Red Group 41B. Petaloid base is Yellow Group 12B.

Reproductive organs:
*Pollen*.—None observed.
*Anthers*.—Size: 2 mm in length. Color: Yellow-Orange Group 22B. Quantity: 65 on average.
*Filaments*.—Color: Yellow-Orange Group 21B. Length: 6 mm.
*Pistils*.—Length: 6 mm. Quantity: 45 on average.
*Stigmas*.—Color: Greyed-Yellow Group 161B.
*Styles*.—Color: Greyed-Yellow Group 161B.
*Location of stigmas*.—Level in location relative to the length of the filaments and the height of the anthers.
*Hips*.—None Observed.

PLANT

Plant growth: Upright. Plants are 50 cm in height, and 50 cm wide.

Stems:
*Color*.—Juvenile growth: Yellow-Green Group 144A. Mature growth: Yellow-Green Group 144A.
*Length*.—Canes are 30 to 40 cm from the base of the plant to the flowering portion.
*Diameter*.—4 to 5 mm.
*Internodes*.—On mature canes, there is an average distance of 42 mm between nodes.
*Surface texture*.—Young wood: Smooth. Older wood: Smooth.

Long prickles:
*Incidence*.—5 prickles per 10 cm of stem.
*Size*.—Average length of prickles on mature stems is 5 mm.
*Shape*.—Upper portion is linear. Lower portion is concave.
*Color*.—Juvenile prickles: Greyed-Purple Group 184C. Mature prickles: Greyed-Purple Group 184C.

Plant foliage:
*Compound leaf*.—130 mm (l)×90 (w).
*Quantity*.—2 leaves per 10 cm of stem on average.
*Leaf bearing angle to the stem*.—45 degrees.
*Color of juvenile foliage*.—Upper side: Yellow-Green Group 146B. Lower side: Yellow-Green Group 146B. Anthocyanin, the color of Greyed-Orange Group 174A, generalized.
*Color of mature foliage*.—Upper side: Yellow-Green Group 146A. Lower side: Yellow-Green Group 146B.

Plant leaves and leaflets:
*Stipules*.—Size: 25 mm in length. Approximately 10 mm wide. Quantity: 2 per compound leaf. Shape: Linear, slightly broad based with outward extending apices apecies. Margins: Finely serrated with stipitate glands. Color: Yellow-Green Group 144A.
*Petiole*.—Length: 30 mm. Diameter: 2 mm.
*Upper surface*.—Color: Yellow-Green Group 144A.
*Lower surface*.—Color: Yellow-Green Group 144B.
*Rachis*.—Length: 40 mm. Upper surface: Color: Yellow-Green Group 144A.
*Lower surface*.—Color: Yellow-Green Group 144B.
*Leaflet*.—Quantity: Normal number of leaflets per leaf leaves in the middle of the stem is 5 leaflets. Margins: Serrated. Size: Average size of the terminal leaflet on normal leaves is 60 mm in length by 40 mm wide. Shape: Generally elliptical. Base: Rounded. Apex: Cuspidate. Texture: Smooth. Thickness: Average. Arrangement: Odd pinnate. Venation: Reticulate. Glossiness: Very glossy.

Disease resistance: Above average resistance to powdery and downy mildew, rust, black spot, and *Botrytis* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

The invention claimed is:

1. A new and distinct variety of rose plant of the Hybrid Tea rose class named 'Poulht007', substantially as illustrated and described herein, due to its abundant orange flowers, disease resistance, and extended period of bloom.

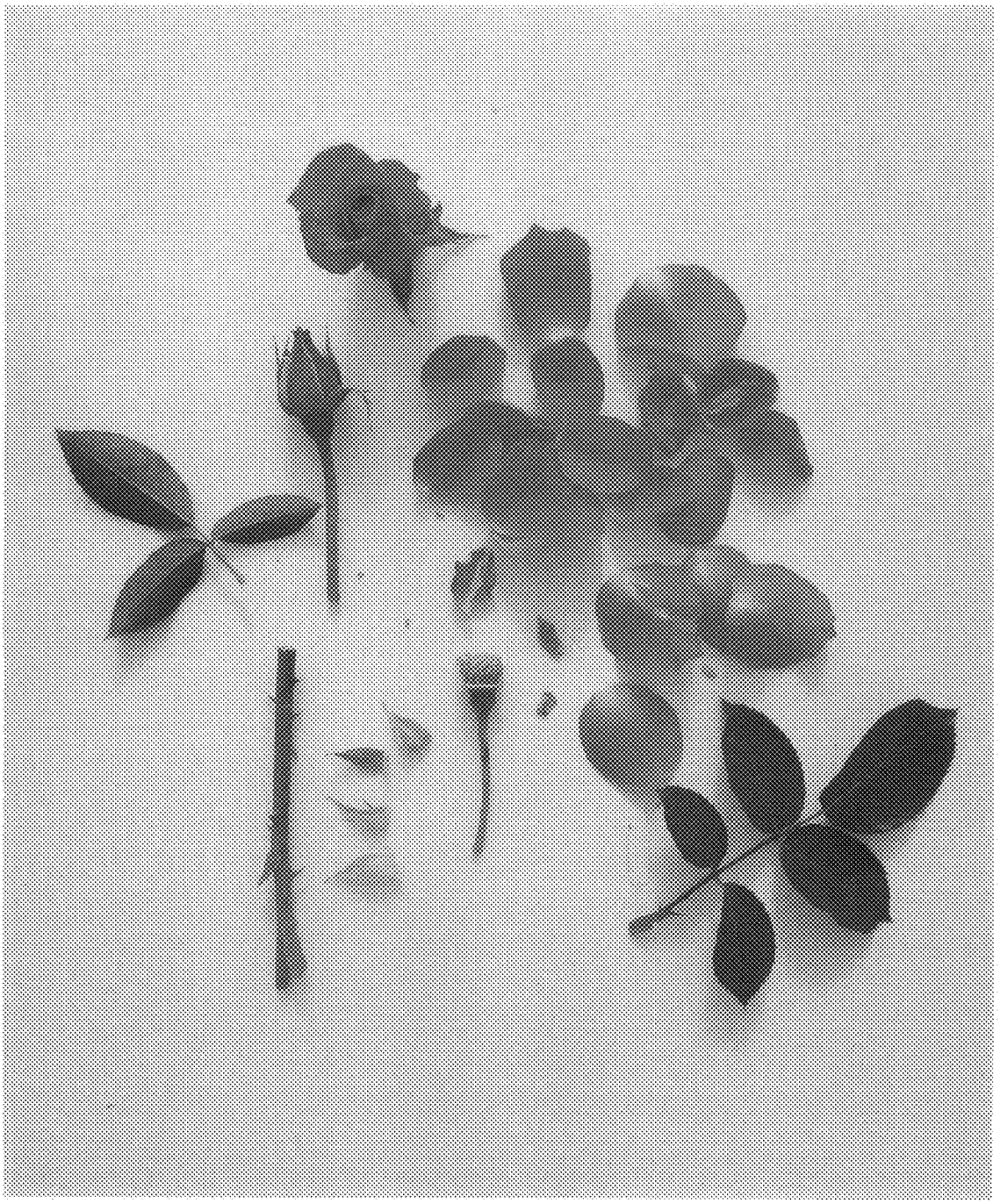

* * * * *